United States Patent
Terry

(10) Patent No.: US 7,139,599 B2
(45) Date of Patent: *Nov. 21, 2006

(54) CEPSTRAL DOMAIN PULSE OXIMETRY

(75) Inventor: Alvin Mark Terry, Longmont, CO (US)

(73) Assignee: Datex-Ohmeda, Inc., Madison, WI (US)

( * ) Notice: Subject to any disclaimer, the term of this patent is extended or adjusted under 35 U.S.C. 154(b) by 156 days.

This patent is subject to a terminal disclaimer.

(21) Appl. No.: 10/714,529

(22) Filed: Nov. 14, 2003

(65) Prior Publication Data

US 2004/0171948 A1    Sep. 2, 2004

Related U.S. Application Data

(63) Continuation of application No. 10/371,658, filed on Feb. 21, 2003, now Pat. No. 6,650,918.

(60) Provisional application No. 60/359,018, filed on Feb. 22, 2002.

(51) Int. Cl.
*A61B 5/00* (2006.01)
*A61B 5/02* (2006.01)

(52) U.S. Cl. ............ 600/336; 600/324; 600/502

(58) Field of Classification Search ........ 600/322–324, 600/310, 330, 336, 481, 500, 502
See application file for complete search history.

(56) References Cited

U.S. PATENT DOCUMENTS 3,566,035 A * 2/1971 Noll et al. ............ 704/203
4,655,228 A   4/1987 Shimura et al.
4,911,167 A   3/1990 Corenman et al. ......... 600/324
5,327,893 A   7/1994 Savic
5,575,285 A   11/1996 Takanashi et al. ......... 600/323
5,677,984 A   10/1997 Mitome .................. 395/2.12
5,766,127 A   6/1998 Pologe et al. ............. 600/310
5,934,277 A   8/1999 Mortz
6,002,952 A * 12/1999 Diab et al. ................ 600/310
6,045,511 A   4/2000 Ott et al. ................... 600/504
6,333,986 B1  12/2001 Petty ....................... 382/103
6,390,986 B1  5/2002 Curcie et al. ............. 600/485
6,650,918 B1 * 11/2003 Terry ....................... 600/336

* cited by examiner

*Primary Examiner*—Eric F. Winakur
(74) *Attorney, Agent, or Firm*—Marsh Fischmann & Breyfogle LLP

(57) ABSTRACT

Processing of plethysmographic signals via the cepstral domain is provided. In one embodiment, a cepstral domain plethysmographic signal processing method (200) includes the steps of obtaining (210) time domain plethysmographic signals, smoothing (220) the time domain plethysmographic signals, performing (230) a first-stage Fourier transformation of the time domain plethysmographic signals to frequency domain plethysmographic signals, computing (240) power spectrums from the frequency domain plethysmographic signals, scaling (250) the power spectrums with a logarithmic function, performing (260) a second-stage Fourier transformation on log-scaled spectrums to transform the power spectrums into cepstrums, and examining (270) the cepstrums to obtain information therefrom relating to a physiological condition of the patient such as the patient's pulse rate or SPO2 level.

20 Claims, 14 Drawing Sheets

CEPSTRAL DOMAIN PULSE OXIMETRY

RELATED APPLICATION INFORMATION

This application is a continuation of and claims priority from U.S. application Ser. No. 10/371,658 entitled "CEPSTRAL DOMAIN PULSE OXIMETRY" filed on Feb. 21, 2003, now U.S. Pat. No. 6,650,918, which claims priority from U.S. Provisional Application Ser. No. 60/359,018 entitled "CEPSTRAL DOMAIN PULSE OXIMETRY" filed on Feb. 22, 2002, the entire disclosures of which are incorporated herein.

FIELD OF THE INVENTION

The present invention relates generally to pulse oximetry, and more particularly to pulse rate and blood analyte level estimation using cepstral domain processing of plethysmographic signals.

BACKGROUND OF THE INVENTION

Current pulse oximeters obtain two signals derived from the attenuation of red and infrared light signals as they are passed through a patient tissue site, typically a finger. A number of processing methods have been developed in the industry in both time and frequency domains to obtain both pulse rate information and the oxygen content (SpO2) level of the arterial blood from the attenuated red and infrared light signals. The attenuated red and infrared signals show a pulsing waveform that is related to the heart rate of the patient. These time domain signals, usually after some bandpass filtering, are used for display of the pulse cycle and are known as plethysmographic signals. Prior techniques for pulse-rate estimation have mostly operated in the time domain and have used peak picking and analysis to derive a pulse rate. Time domain measures can respond quickly to pulse rate changes, but the presence of moderate motion and/or low amplitude pulses pose problems for accurate peak picking. Processing in the frequency or spectral domain has also been used and this requires a longer sample of the waveform to generate a pulse estimate. Also, identification of the predominant spectral peak produced by the pulse can be problematic in the presence of motion artifacts.

SUMMARY OF THE INVENTION

Accordingly, the present invention provides for processing of plethysmographic signals via the cepstral domain to enhance the determination of patient physiological condition related information such as patient pulse rate and SPO2 level information from plethysmographic signals, especially when motion artifacts are present in the plethysmographic signals. In accordance with the present invention, plethysmographic signals (e.g., attenuated red and infrared signals) are sampled and transformed into the cepstral domain, via, for example, a logarithmic like transform sandwiched between two forward Fourier transforms. Peaks in the cepstral domain are related primarily to the pulse rate. Identification of the pulse generated cepstral domain peak allows for pulse estimation in the presence of moderate motion artifacts. The cepstral information also allows for adaptive filtering of the input plethysmographic signals to remove noise and artifacts. The relative magnitudes of the cepstral peaks for both red and infrared signals in conjunction with an estimate of the DC levels of the red and infrared signals also allows for measurement of blood analyte (e.g., SPO2) levels of the blood.

According to one aspect of the present invention, a method of processing at least first and second time domain plethysmographic signals (e.g., red and infrared plethysmographic signals) obtained from a patient includes the steps of performing a Fourier transformation on the first time domain plethysmographic signal to transform the first plethysmographic signal into a first frequency domain plethysmographic signal and performing a Fourier transformation on the second time domain plethysmographic signal to transform the second plethysmographic signal into a second frequency domain plethysmographic signal. In this regard, the Fourier transformations may be fast Fourier transforms. A first power spectrum is computed from the first frequency domain plethysmographic signal and a second power spectrum is computed from the second frequency domain plethysmographic signal. A Fourier transformation is performed on the first power spectrum to transform the first power spectrum into a first cepstrum and a Fourier transformation is performed on the second power spectrum to transform the second power spectrum into a second cepstrum. In this regard, the Fourier transformations may be fast Fourier transforms. The first and second cepstrums are then examined to obtain information therefrom relating to a physiological condition of the patient.

The physiological condition of the patient may, for example, be the patient's pulse rate. In this regard, the first and second cepstrums may be examined to identify peaks in the first and second cepstrums associated with the pulse rate of the patient, and the pulse rate of the patient may be estimated based on the locations of the identified peaks in the first and second cepstrums.

The physiological condition of the patient may also, for example, be the patient's SPO2 level. In this regard, DC levels of the first and second power spectrums may be determined, AC levels of the first and second time domain plethysmographic signals may be determined from the identified peaks in the first and second cepstrums, and a value correlated with a blood analyte level (e.g., SPO2 level) of the patient may be computed from the DC values of the first and second power spectrums and the AC levels of the first and second time domain plethysmographic signals.

According to another aspect of the present invention, a method of determining a pulse rate of a patient from at least one time domain plethysmographic signal obtained from the patient includes the step of obtaining a time domain based estimate of the pulse rate of the patient from the time domain plethysmographic signal. The time domain plethysmographic signal is transformed to a spectral domain plethysmographic signal and a spectral domain based estimate of the pulse rate of the patient is obtained from the spectral domain plethysmographic signal. The spectral domain plethysmographic signal is transformed to a cepstral domain plethysmographic signal and a cepstral domain based estimate of the pulse rate of the patient is obtained from the cepstral domain plethysmographic signal. A best estimate of the pulse rate of the patient is then determined based on at least the time, spectral, and cepstral domain based estimates of the pulse rate of the patient.

According to one more aspect of the present invention, a pulse oximeter includes first and second optical signal sources operable to emit optical signals characterized by first and second wavelengths (e.g., red and infrared), respectively. The pulse oximeter also includes a drive system, a detector, a digital sampler (e.g., an analog-to-digital converter), and a digital processor. The drive system is operable to cause operation of the first and second optical signal sources such that each optical signal source emits first and second optical signals, respectively, in accordance with a multiplexing method. The detector is operable to receive the first and second optical signals after the first and second optical signals are attenuated by a patient tissue site of a patient. The detector is also operable to provide an analog detector output signal representative of the attenuated first and second optical signals. The digital sampler is operable to sample the analog detector output signal at a desired sampling rate and output a digital signal having a series of sample values representative of the attenuated first and second optical signals. The digital processor is enabled to demultiplex the series of sample values into first and second time domain plethysmographic signals, transform the first and second time domain plethysmographic signals into first and second spectral domain signals, transform the first and second spectral domain plethysmographic signals into first and second cepstral domain plethysmographic signals, and examine the first and second cepstral domain plethysmographic signals to obtain information therefrom relating to a physiological condition of the patient, such as the patient's pulse rate or SPO2 level.

According to a further aspect of the present invention, a pulse arbitration method for use in determining a fundamental pulse frequency (or pulse rate) of a patient from multiple signal domains (e.g., time, energy, log, and cepstral) associated with at least one time domain plethysmographic signal obtained from the patient includes the step of transforming the time domain plethysmographic signal to a spectral domain plethysmographic signal. The spectral domain plethysmographic signal is transformed to a cepstral domain plethysmographic signal. The transformations to the spectral and cepstral domains may, for example, be accomplished via Fourier transformation operations. The spectral and cepstral domain plethysmographic signals are examined to identify corresponding spectral and cepstral domain plethysmographic signal peaks. The identified corresponding spectral and cepstral domain plethysmographic signal peaks are then used to select the fundamental pulse frequency from among a plurality of possible candidates for the fundamental pulse frequency of the patient. Possible candidates for the fundamental pulse frequency of the patient may, for example, be obtained from the time, spectral, and/or cepstral domain plethysmographic signals as well as from a filtered time domain plethysmographic signal and/or a log scaled spectral domain plethysmographic signal.

Cepstral domain processing of plethysmographic signals offers several advantages for pulse-rate identification. For example, the log-like transform acts to suppress weaker noise components making peak identification easier, and the cepstral peak is primarily generated via the harmonic components of the pulse so that noise energy surrounding this "fundamental" pulse frequency does not adversely effect pulse frequency identification.

These and other aspects and advantages of the present invention will be apparent upon review of the following Detailed Description when taken in conjunction with the accompanying figures.

DESCRIPTION OF THE DRAWINGS

For a more complete understanding of the present invention and further advantages thereof, reference is now made to the following Detailed Description, taken in conjunction with the drawings, in which.

DETAILED DESCRIPTION

Figure 1:
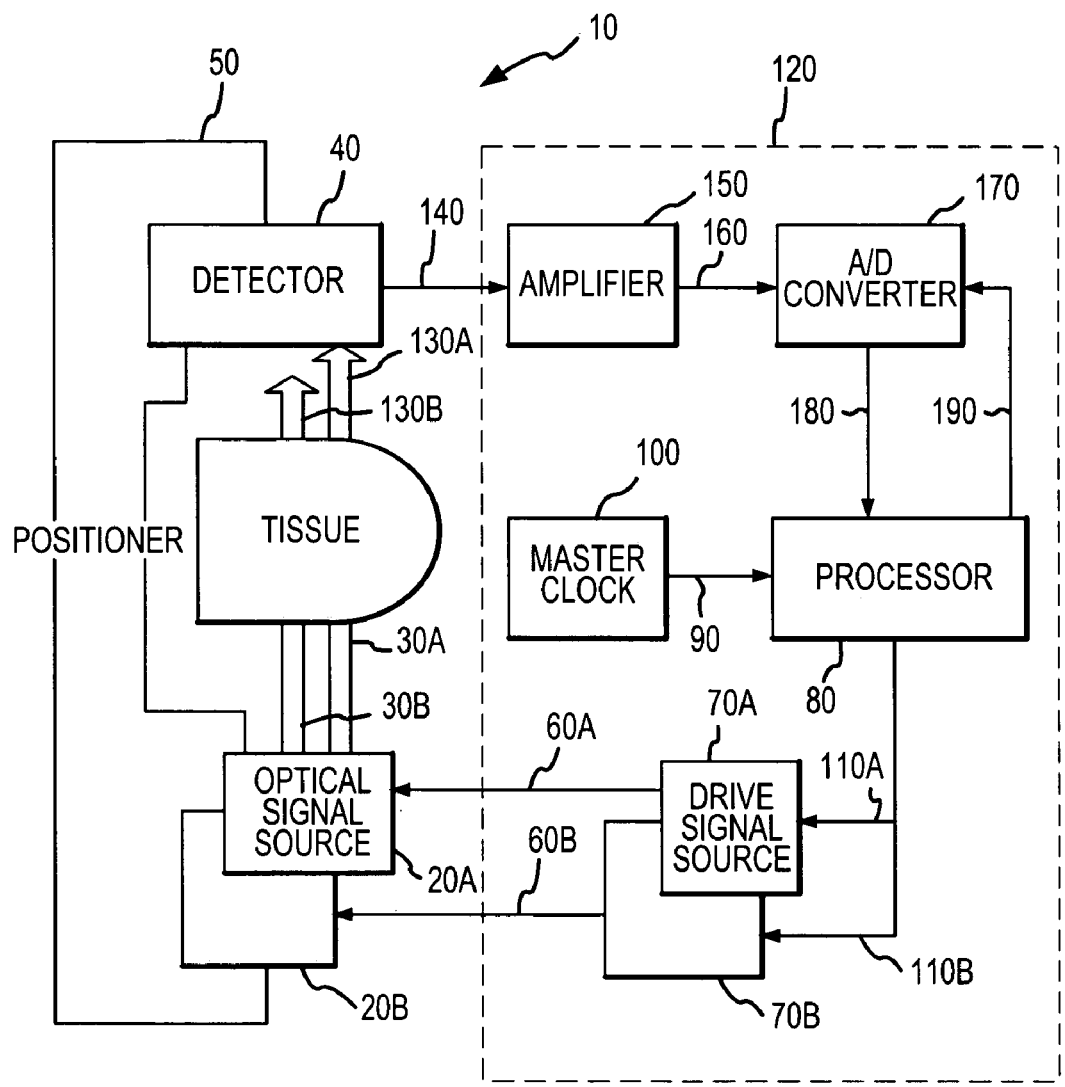
FIG. 1 is a block diagram of one embodiment of a pulse oximeter in which a cepstral domain plethysmographic signal processing method in accordance with the present invention may be implemented.

Referring now to FIG. 1, there is shown a block diagram of one embodiment of a pulse oximeter 10 in which a cepstral domain plethysmographic signal processing method in accordance with the present invention may be implemented. The pulse oximeter 10 is configured for use in determining the pulse rate of a patient as well as one or more blood analyte levels in the patient, such as an SPO2 level. It should be appreciated that a cepstral domain plethysmographic signal processing method in accordance with the present invention may be implemented in pulse oximeters that are configured differently from the pulse oximeter depicted in FIG. 1 as well as in other environments wherein plethysmographic signals are processed in order to obtain desired information relating to patient physiological conditions from the plethysmographic signals.

The pulse oximeter 10 includes a pair of optical signal sources 20a, 20b for emitting a corresponding pair of light signals 30a, 30b centered at different predetermined center wavelengths $\lambda_1$, $\lambda_2$ through a suitable tissue site of a patient and on to a detector 40 (e.g., a photo-sensitive diode). The optical signal sources 20a, 20b and detector 40 may be included in a positioning device 50, or probe, to facilitate alignment of the light signals 30a, 30b with the detector 40. For example, the positioning device 50 may be of clip-type or flexible strip configuration adapted for selective attachment to a suitable patient tissue site (e.g., a finger, an ear lobe, a foot, or the nose of the patient). The center wavelengths $\lambda_1$, $\lambda_2$ required depend upon the blood analyte level to be determined. For example, in order to determine an SPO2 level, $\lambda_1$ may be in the Red wavelength range and $\lambda_2$ may be in the infrared wavelength range. It should be appreciated that the pulse oximeter 10 may be readily implemented with more optical signal sources (e.g., four) depending upon the number of different blood analyte levels to be measured.

The optical signal sources 20a, 20b are activated by a corresponding plurality of drive signals 60a, 60b to emit the light signals 30a, 30b. The drive signals 60a, 60b are supplied to the optical signal sources 20a, 20b by a corresponding plurality of drive signal sources 70a, 70b. The drive signal sources 70a, 70b may be connected with a digital processor 80, which is driven with a clock signal 90 from a master clock 100. The digital processor 80 may be programmed to define modulation waveforms, or drive patterns, for each of the optical signal sources 20a, 20b. More particularly, the digital processor 80 may provide separate digital trigger signals 110a, 110b to the drive signal sources 70a–d, which in turn generate the drive signals 60a, 60b. In this regard, the digital trigger signals 110a, 110b may be configured to provide for multiplexing of the drive signals 60a, 60b, and in turn the light signals 30a, 30b, in accordance with a multiplexing scheme (e.g., time division, frequency division, or code division multiplexing).

The drive signal sources 70a, 70b, processor 80 and clock 100 may all be housed in a monitor unit 120. While the illustrated embodiment shows the optical signal sources 20a, 20b physically interconnected with the positioning device 50 (e.g., mounted within the positioning device 50 or mounted within a connector end of a cable that is selectively connectable with the positioning device 50), it should be appreciated that the optical signal sources 20a, 20b may also be disposed within the monitor unit 120. In the latter case, the light signals 30a, 30b emitted from the optical signal sources 20a, 20b may be directed from the monitor unit 120 via one or more optical fibers to the positioning device 50 for transmission through the tissue site. Furthermore, the drive signal sources 70a, 70b may comprise a single drive signal generator unit that supplies each of the drive signals 60a, 60b to the optical signal sources 20a, 20b.

Transmitted light signals 130a, 130b (i.e., the portions of light signals 30a, 30b exiting the tissue) are detected by the detector 40. The detector 40 detects the intensities of the transmitted signals 130a, 130b and outputs a current signal 140 wherein the current level is indicative of the intensities of the transmitted signals 130a, 130b. As may be appreciated, the current signal 140 output by the detector 40 comprises a multiplexed signal in the sense that it is a composite signal including information about the intensity of each of the transmitted signals 130a, 130b. Depending upon the nature of the drive signals 60a, 60b, the current signal 140 may, for example, be time division multiplexed, wavelength division multiplexed, or code division multiplexed.

The current signal 140 is directed to an amplifier 150, which may be housed in the monitor unit 120 as is shown. As an alternative, the amplifier 150 may instead be included in a probe/cable unit that is selectively connectable with the monitor unit 120. The amplifier 150 converts the current signal 140 to a voltage signal 160 wherein a voltage level is indicative of the intensities of the transmitted signals 130a, 130b. The amplifier 150 may also be configured to filter the current signal 140 from the detector 40 to reduce noise and aliasing. By way of example, the amplifier 150 may include a bandpass filter to attenuate signal components outside of a predetermined frequency range encompassing modulation frequencies of the drive signals 60a, 60b.

Since the current signal 140 output by the detector 40 is a multiplexed signal, the voltage signal 160 is also a multiplexed signal, and thus, the voltage signal 160 must be demultiplexed in order to obtain signal portions corresponding with the intensities of the transmitted light signals 130a, 130b. In this regard, the digital processor 80 may be provided with demodulation software for demultiplexing the voltage signal 160. In order for the digital processor 80 to demodulate the voltage signal 160, it must first be converted from analog to digital. Conversion of the analog voltage signal 160 is accomplished with an analog-to-digital (A/D) converter 170, which may also be included in the monitor unit 120. The A/D converter 170 receives the analog voltage signal 160 from the amplifier 150, samples the voltage signal 160, and converts the samples into a series of digital words 180 (e.g., eight, sixteen or thirty-two bit words), wherein each digital word is representative of the level of the voltage signal 160 (and hence the intensities of the transmitted light signals 130a, 130b) at a particular sample instance. In this regard, the A/D converter 170 should provide for sampling of the voltage signal 160 at a rate sufficient to provide for accurate tracking of the shape of the various signal portions comprising the analog voltage signal 160 being converted. For example, the A/D converter 170 may provide for a sampling frequency at least twice the frequency of the highest frequency drive signal 60a, 60b, and typically at an even greater sampling rate in order to more accurately represent the analog voltage signal.

The series of digital words 180 is provided by the A/D converter 170 to the processor 80 to be demultiplexed. More particularly, the processor 80 may periodically send an interrupt signal 190 (e.g., once per every eight, sixteen or thirty-two clock cycles) to the A/D converter 170 that causes the A/D converter 170 to transmit one digital word 180 to the processor 80. The demodulation software may then demultiplex the series of digital words 180 in accordance with an appropriate method (e.g., time, wavelength, or code) to obtain digital signal portions indicative of the intensities of each of the transmitted light signals 130a, 130b. In this regard, the demultiplexed digital signal portions comprise time domain plethysmographic signals corresponding to the center wavelengths $\lambda_1$, $\lambda_2$ (e.g., red and infrared) of the optical signal sources 20a, 20b. The red and infrared time domain plethysmographic signals may then be processed by the processor 80 to obtain desired patient physiological condition related information therefrom such as the patient's pulse rate and SPO2 level.

Figure 2:
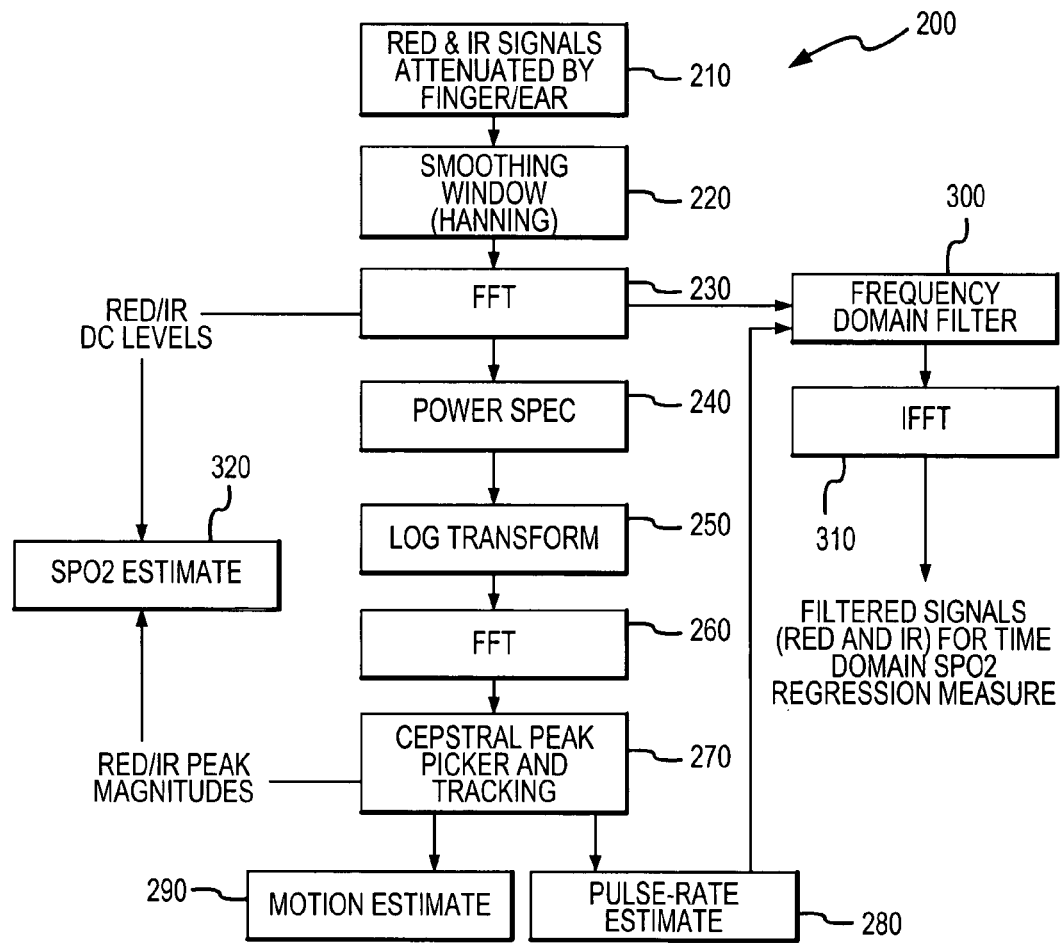
FIG. 2 is a block diagram showing one embodiment of a method for processing plethysmographic signals via the cepstral domain in accordance with the present invention.
Figure 3A:
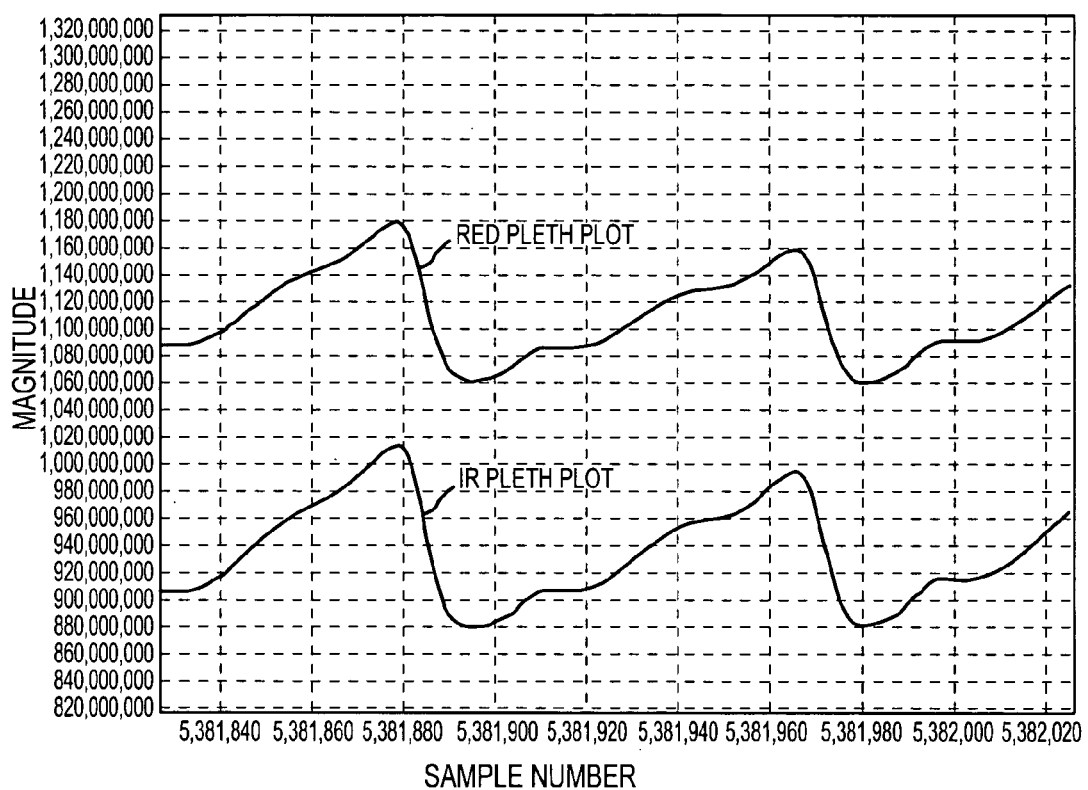
FIG. 3A is a plot showing typical red and infrared time domain plethysmographic input signals to be processed in accordance with the steps of FIG. 2.

Referring now to FIG. 2 there is shown a block diagram illustrating one embodiment of a method (200) for processing the red and infrared time domain plethysmographic signals via the cepstral domain to obtain desired information relating to patient physiological conditions such as patient pulse rate and blood analyte level (e.g., SPO2) information. The cepstral domain plethysmographic signal processing method (200) begins with obtaining (210) two digitized time domain plethysmographic signals such as red and infrared plethysmographic signals. In this regard, typical red and infrared time domain plethysmographic signals that have been sampled at 50 Hz are shown in FIG. 3A. The cepstral domain processing method (200) is particularly suited for implementation in software executable by the digital processor 80 of a pulse oximeter 10 such as described above in connection with FIG. 1. In other embodiments, the cepstral domain processing method (200) may be configured for processing non-digitized plethysmographic signals and may be implemented in appropriate hardware components. Furthermore, the cepstral domain processing method (200) may be configured for simultaneously processing more than two plethysmographic signals.

Figure 3B:
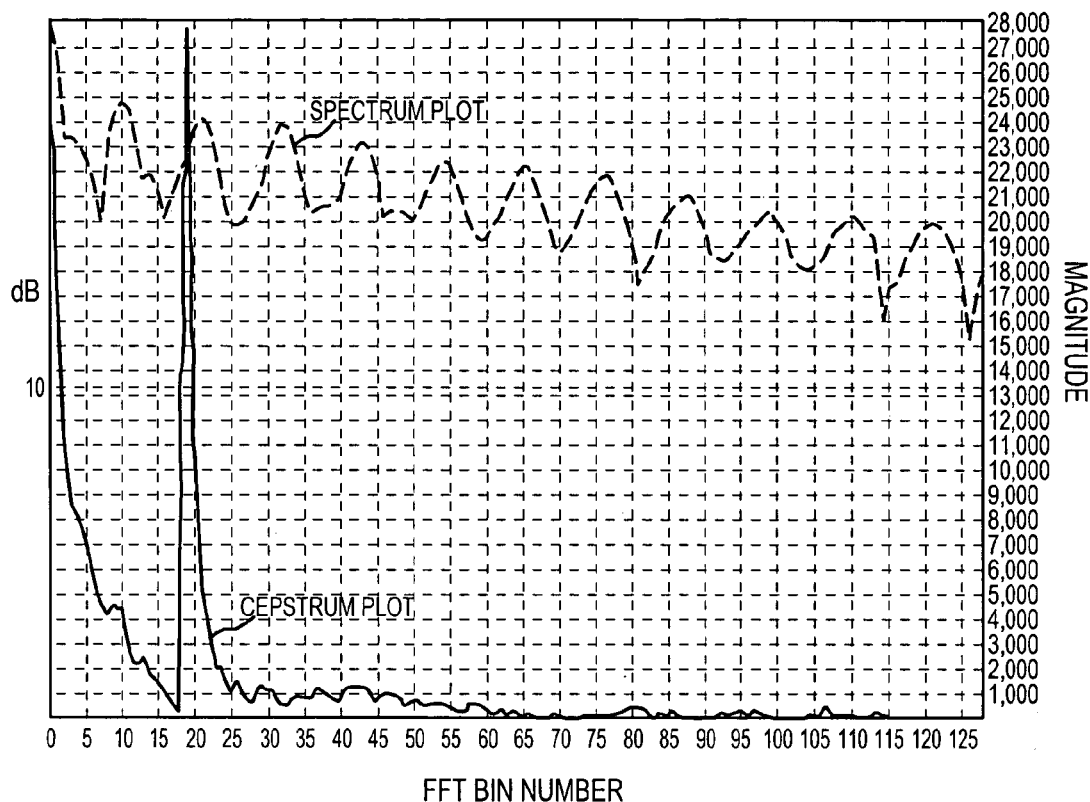
FIG. 3B is a plot showing the Spectrum and Cepstrum for the red plethysmographic input signal of FIG. 3A after processing in accordance with the steps of FIG. 2.
Figure 3C:
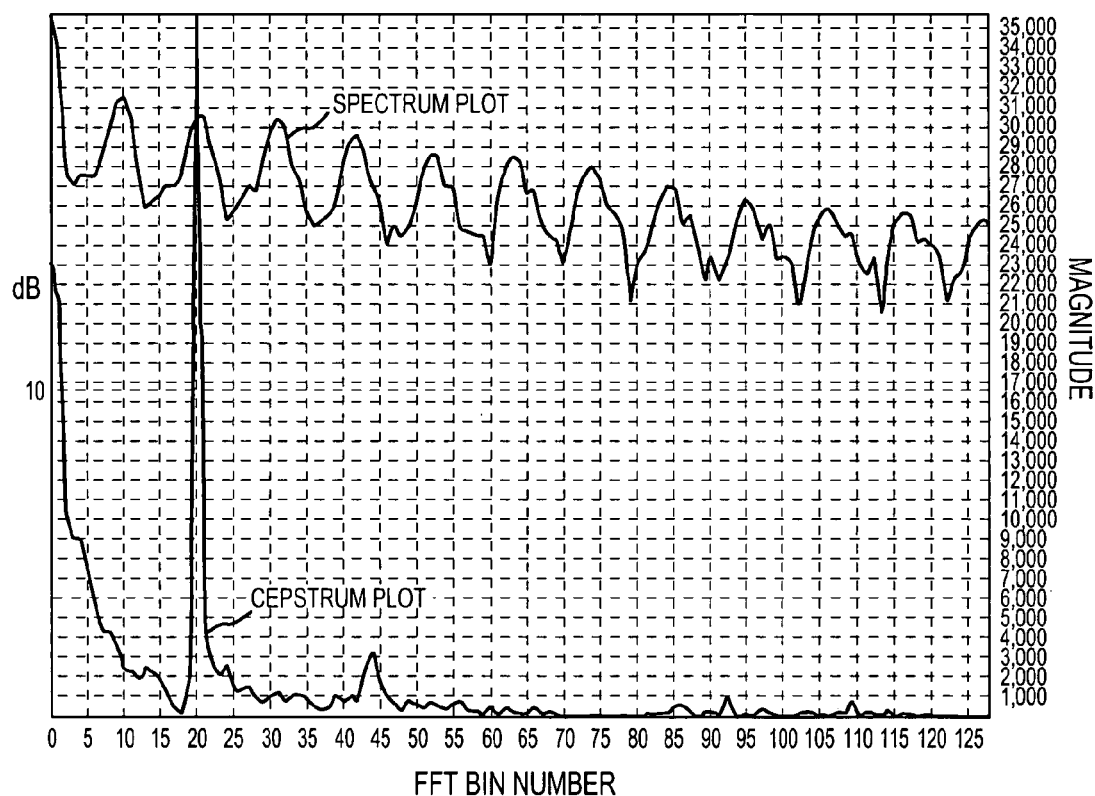
FIG. 3C is a plot showing the Spectrum and Cepstrum for the infrared plethysmographic input signal of FIG. 3A after processing in accordance with the steps of FIG. 2.

A suitable smoothing window function (e.g., Hanning, Hamming, Kaiser) is applied (220) to the digitized time domain plethysmographic signals to smooth the signals. Smoothing the digitized time domain plethysmographic signals achieves improved frequency estimation. After the signals are smoothed, a first Fourier transformation operation is performed (230) on the signals to transform the red and infrared plethysmographic signals from the time domain to the frequency domain. Since there are two primary signals (the red and infrared inputs), it is convenient to perform the first Fourier transformation of the signals in parallel using a complex Fast Fourier Transform (FFT) procedure. If desired, the results of the FFT calculations may be appropriately scaled (e.g., by dividing by the number of points used in the FFT calculations) to help prevent floating point overflow errors in subsequent computations. After the first stage FFT is performed, respective power spectrums are computed (240) from the frequency domain red and infrared plethysmographic signals. In this regard, the power spectrums may be computed (240) by squaring and summing the appropriate real and imaginary frequency components of the red and infrared frequency domain plethysmographic signals. Power spectrums of the typical red and infrared plethysmographic signals after the first stage FFT are shown in FIGS. 3B and 3C, respectively.

After the power spectrums are computed, a log-like or companding function is applied (250) to the red and infrared power spectrums. Application of the log-like or companding function suppresses smaller noise components and emphasizes the prominent harmonics so that periodicity in the spectrum is more easily extracted. A second Fourier transformation operation is then performed (260) on the log transformed power spectrums to transform the signals to the cepstral domain. In this regard, it is convenient to perform the second-stage Fourier transformation of the log scaled power spectrums in parallel using a complex Fast Fourier Transform (FFT) procedure. If desired, the results of the second-stage FFT calculations may be appropriately scaled in a manner similar to scaling done on the results of the first-stage FFT calculations. The cepstrums of the typical red and infrared plethysmographic signals obtained after the second stage FFT are also shown in FIGS. 3B and 3C, respectively.

Once the red and infrared cepstrums are obtained, the separate red and infrared cepstrums are then examined (270) for peaks associated with the pulse rate of the patient. In this regard, the most prominent (i.e., largest amplitude) peak in each cepstrum may be identified. The location of the most prominent peak in each cepstrum provides an indication of the fundamental frequency of the plethysmographic waveform from which the cepstrum is obtained. Since the fundamental frequency of a plethysmographic waveform is proportional to the patient's pulse rate, the pulse rate of the patient may be estimated (280) from one or both of the cepstrums. For example, the most prominent peak in the red cepstrum of FIG. 3B occurs at around the 20th bin of the FFT spectrum corresponding to a cepstral based pulse rate estimate of approximately 65 beats-per-minute. It should be noted that this estimate differs slightly from a conventional time domain based estimate obtained from the time domain red plethysmographic waveform shown in FIG. 3A of 61 beats-per-minute. Pulse-rate estimates may be obtained from both the red and infrared cepstrums and the separate estimates may be correlated with one another in order to obtain a single estimate of the patient's pulse rate. Further, while it is possible to estimate the patient's pulse rate based only on information from one or both of the cepstrums, a time domain based estimate of the patient's pulse rate may also be used for initial identification purposes and to support subsequent tracking of the cepstral peak (Quefrency) associated with the pulse rate.

Figure 3D:
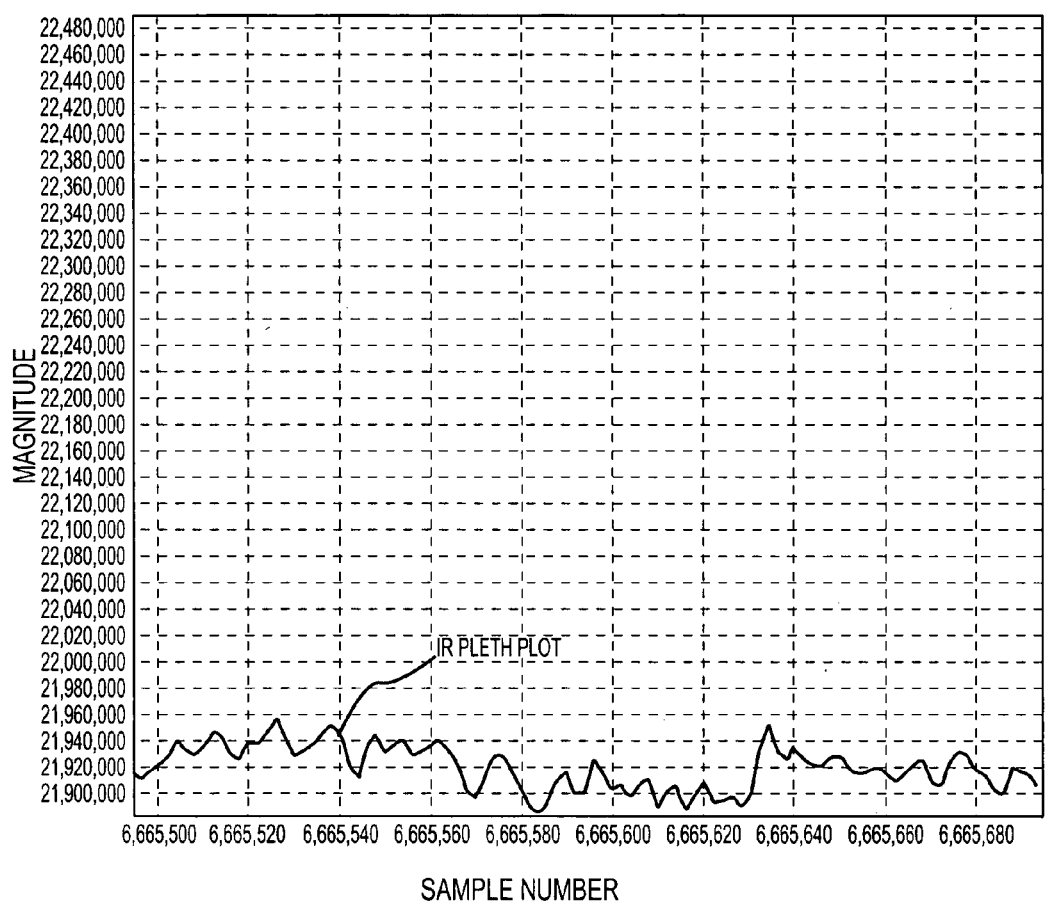
FIG. 3D is a plot showing a typical infrared time domain plethysmographic input signal wherein the pulse oximeter probe is not transmitting properly through a patient tissue site (e.g., where the probe is removed from the patient's finger)
Figure 3E:
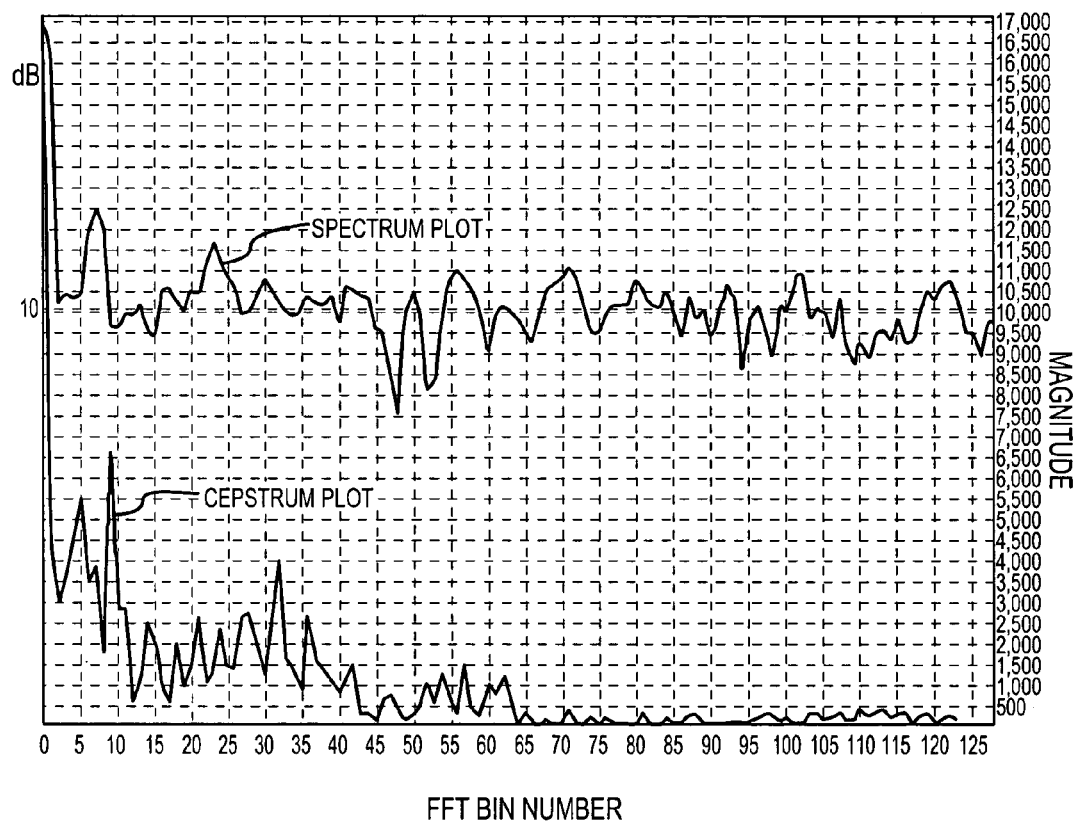
FIG. 3E is a plot showing the Spectrum and Cepstrum for the infrared plethysmographic signal of FIG. 3D after processing in accordance with the steps of FIG. 2.

In some cases, there may not be a prominent peak in one or both of the cepstrums. For example, FIG. 3D shows an infrared time domain plethysmographic signal typical of the situation where there is no physiological signal condition (e.g., where the plethysmographic probe has been removed from the patient's finger), and FIG. 3E shows the infrared power spectrum and cepstrum obtained for the infrared time domain plethysmographic signal of FIG. 3D. While the power spectrum of FIG. 3E differs somewhat from a power spectrum that is typical of a patient physiological signal condition such as the power spectrums shown in FIGS. 3B and 3C, the lack of a patient physiological signal condition is particularly apparent from examination of the cepstrum since there is no prominent peak present in the cepstrum of FIG. 3E as compared with the quite prominent cepstral peaks in FIGS. 3B and 3C.

In addition to examining the cepstrums for peaks associated with patient pulse rate, in step (270) the red and infrared cepstrums may be examined for peaks associated with motion artifacts. Typically, peaks in the red and infrared cepstrums that are associated motion artifacts will be less prominent than the peaks associated with the patient pulse rate. The location(s) of less prominent peaks in each cepstrum provide an indication regarding motion artifacts present in the plethysmographic waveform from which the cepstrum is obtained, and based on this information the frequencies of motion artifacts present in the red and infrared plethysmographic signals may be estimated (290).

Once an estimate of the pulse rate is obtained, the pulse rate information may be used to construct a filter to remove noise and motion artifacts from the input red and infrared signals. This may be done via an adaptive bandpass filter applied in the time domain to the red and infrared signals where the cut off frequencies are determined by the pulse frequency which is identified in the cepstral domain. Alternatively, as is shown in the embodiment of FIG. 2, the frequency domain red and infrared plethysmographic signals may be filtered (300) in the frequency domain after the first stage FFT with a frequency domain filter constructed using the pulse frequency information obtained from the cepstral domain. An inverse fast Fourier transform (IFFT) operation may be performed (310) on the filtered frequency domain signals to obtain filtered time domain red and infrared plethysmographic signals for use in subsequent measures such as a regression based SPO2 estimation which uses the time domain version of the red and infrared inputs signals. Noise removal from the red and infrared signals improves subsequent measures such as regression based SPO2 estimation.

Additionally, the information in both the spectral and cepstral domains may be used to derive an SPO2 measure. The overall DC levels of the red and infrared plethysmographic signals can be determined from the first stage spectrums and the relative magnitudes of the cepstral peaks corresponding to the pulse rate frequency may be used to obtain a measure of the AC levels of the red and infrared plethysmographic signals. In this regard, the following computation may be utilized:

$$R'=AC(\text{cepstral-red})/DC(\text{spectral-red})/AC(\text{cepstral-IR})/DC(\text{spectral-IR})$$

or, expressed in an alternative manner:

$$R'=AC(\text{cepstral-red})/DC(\text{spectral-red})*DC(\text{spectral-IR})/AC(\text{cepstral-IR})$$

where AC(cepstral-red) is the AC level of the red plethysmographic signal obtained from the red cepstrum, DC(spectral-red) is the DC level of the red plethysmographic signal obtained from the red spectrum, AC(cepstral-IR) is the AC level of the infrared plethysmographic signal obtained from the infrared cepstrum, and DC(spectral-IR) is the DC level of the infrared plethysmographic signal obtained from the infrared spectrum. The derived measure R' may then be used to estimate (320) the patient's SPO2 level in a manner similar to known regression techniques where AC and DC estimates are obtained from the time domain red and infrared signals. An example of such a known regression technique is described in U.S. Pat. No. 5,934,277 entitled "SYSTEM FOR PULSE OXIMETRY SPO2 DETERMINATION", the entire disclosure of which is incorporated herein.

Figure 4:
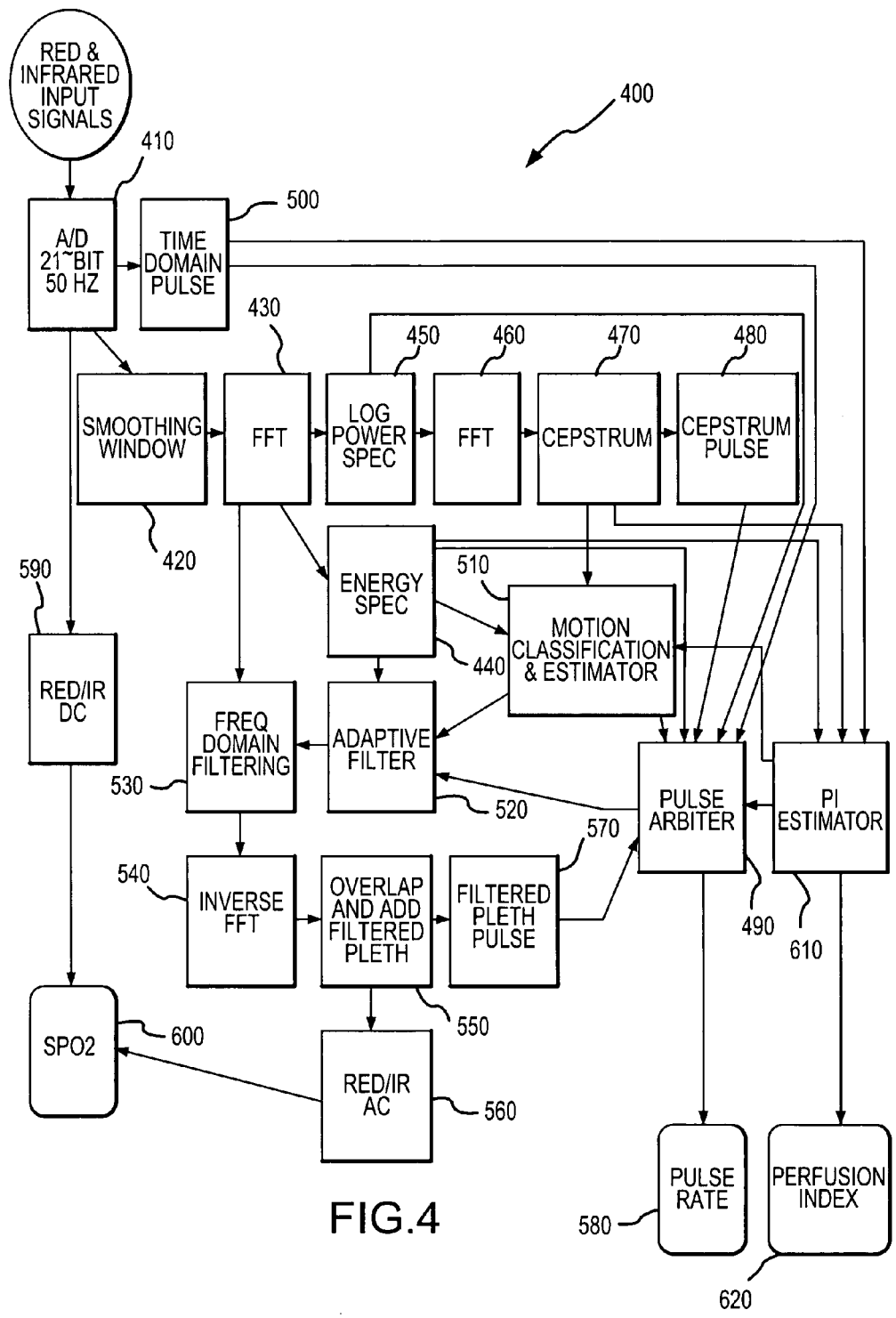
FIG. 4 is a block diagram showing another embodiment of a method for processing plethysmographic signals via the cepstral domain in accordance with the present invention.
Figure 5A:
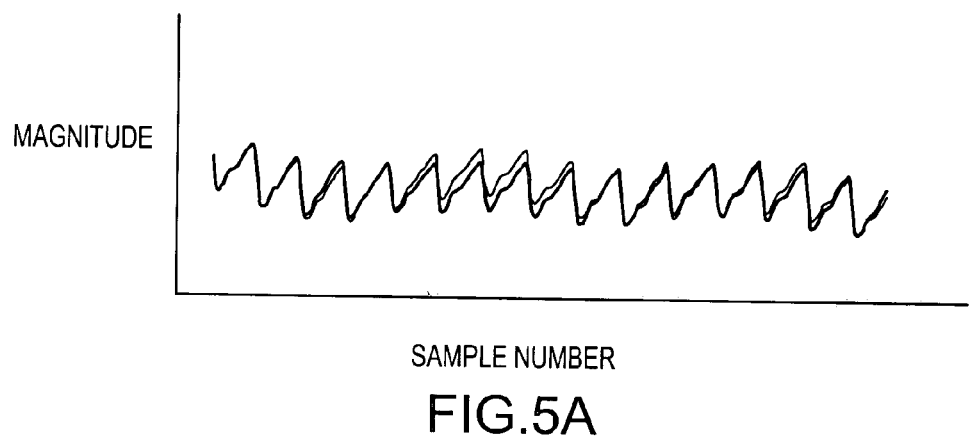
FIG. 5A is a plot showing typical red and infrared time domain plethysmographic input signals to be processed in accordance with the steps of FIG. 4.
Figure 6A:
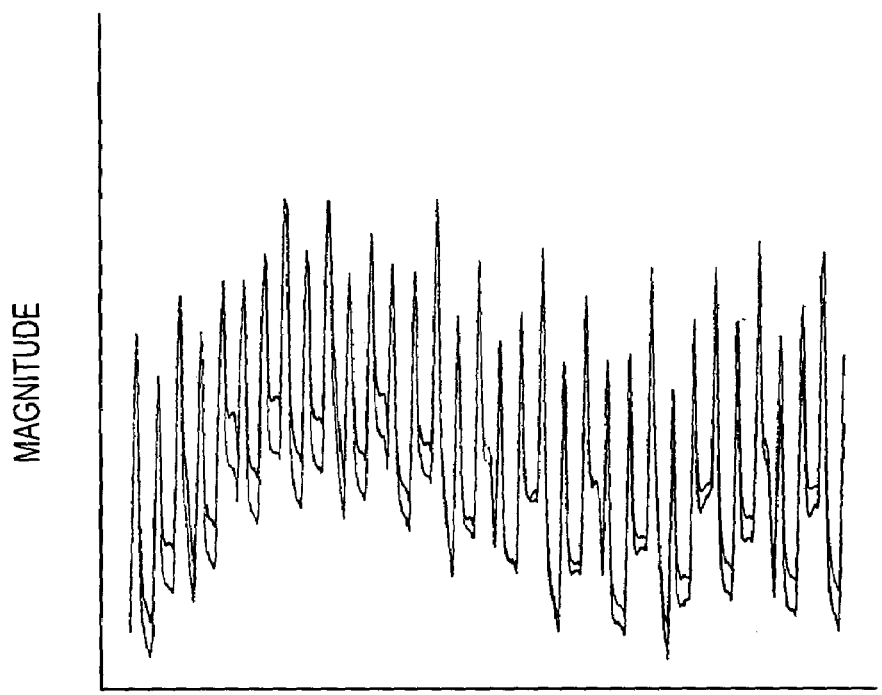
FIG. 6A is a plot showing typical red and infrared time domain plethysmographic input signals to be processed in accordance with the steps of FIG. 4 that include motion induced noise components at a main motion frequency of about 200 bpm.

Referring now to FIG. 4 there is shown a block diagram illustrating another embodiment of a method (400) for processing the red and infrared time domain plethysmographic signals via the cepstral domain to obtain desired information relating to patient physiological conditions such as patient pulse rate and blood analyte level (e.g., SPO2) information. The cepstral domain plethysmographic signal processing method (400) shown in FIG. 4 proceeds in a manner similar to the method (200) shown in FIG. 2. In this regard, two continuous time domain plethysmographic signals such as red and infrared plethysmographic signals are digitized (410) by sampling the signals at a suitable frequency. Typical red and infrared time domain plethysmographic signals that have been sampled at 50 Hz are shown in FIGS. 5A and 6A, with the signals of FIG. 6A including motion artifacts. As with the method (200) of FIG. 2, the cepstral domain processing method (400) is particularly suited for implementation in software executable by the digital processor 80 of a pulse oximeter 10 such as described above in connection with FIG. 1, and in other embodiments, the cepstral domain processing method (400) may be configured for processing non-digitized plethysmographic signals and may be implemented in appropriate hardware components. Furthermore, the cepstral domain processing method (400) may be configured for simultaneously processing more than two plethysmographic signals.

Figure 5B:
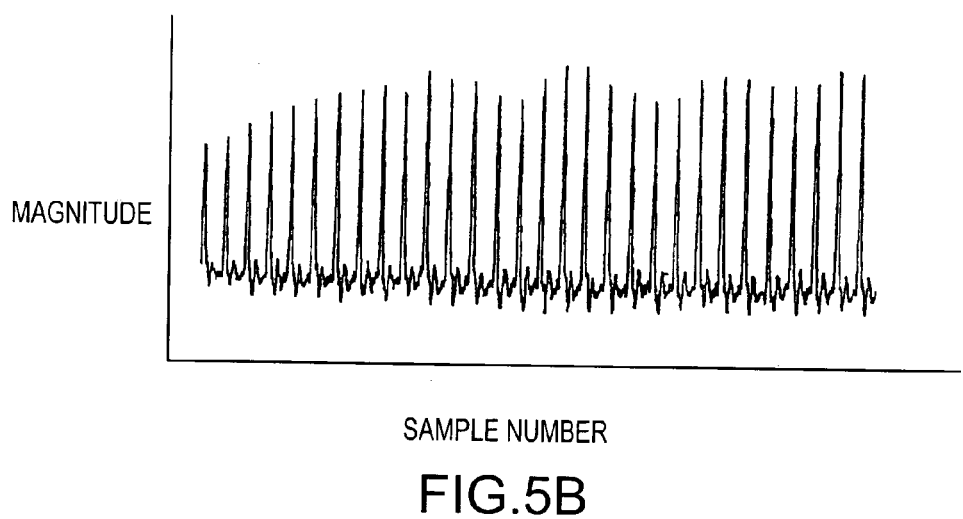
FIG. 5B is a plot showing differentiated waveforms obtained from the typical red and infrared time domain plethysmographic input signals shown in FIG. 5A.
Figure 5C:
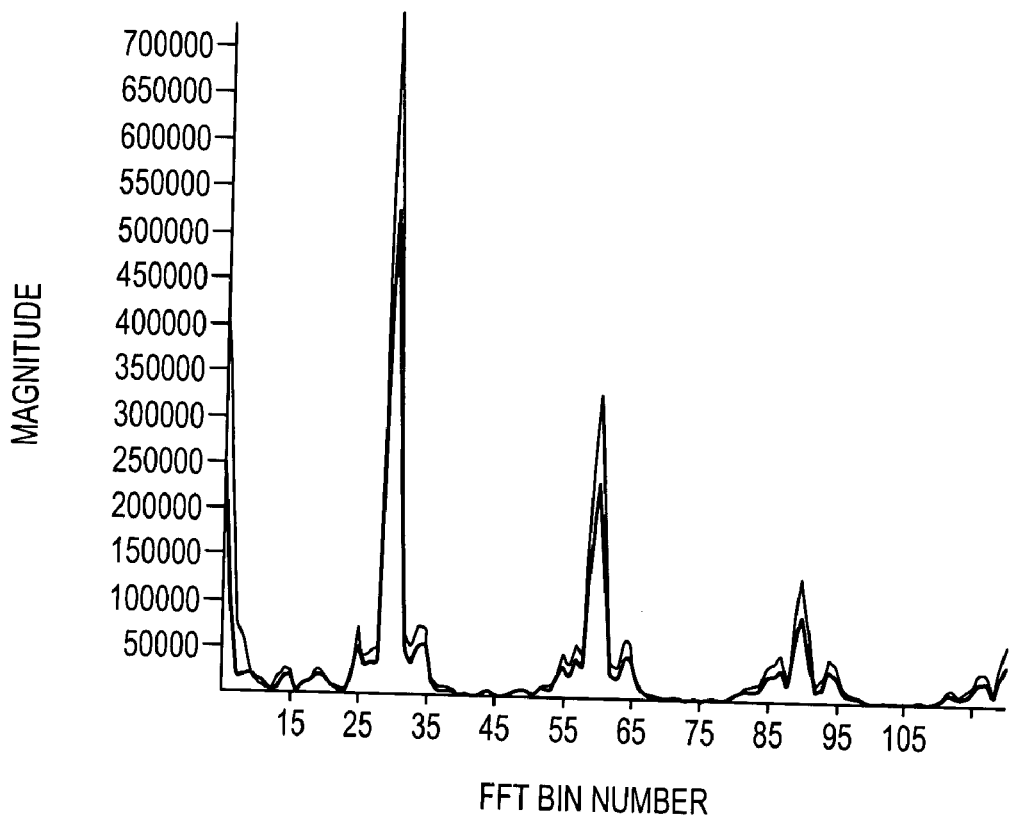
FIG. 5C is a plot showing red and infrared energy spectra corresponding to the typical red and infrared time domain plethysmographic input signals shown in FIG. 5A.
Figure 5D:
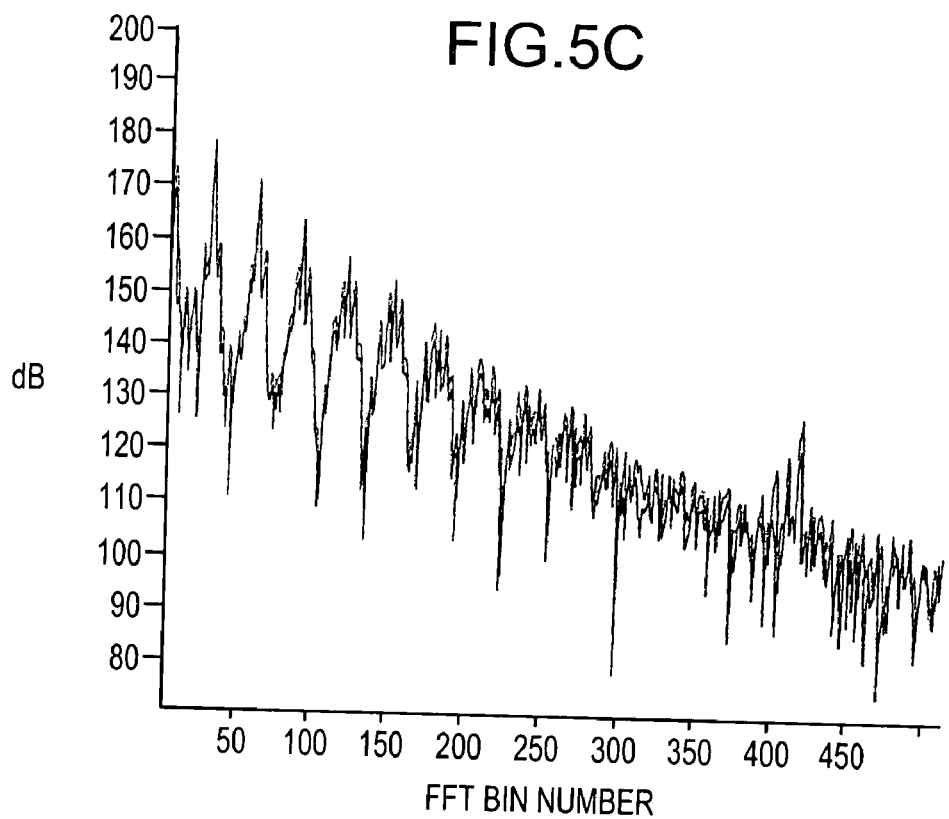
FIG. 5D is a plot showing red and infrared log spectra corresponding to the typical red and infrared time domain plethysmographic input signals shown in FIG. 5A.
Figure 5E:
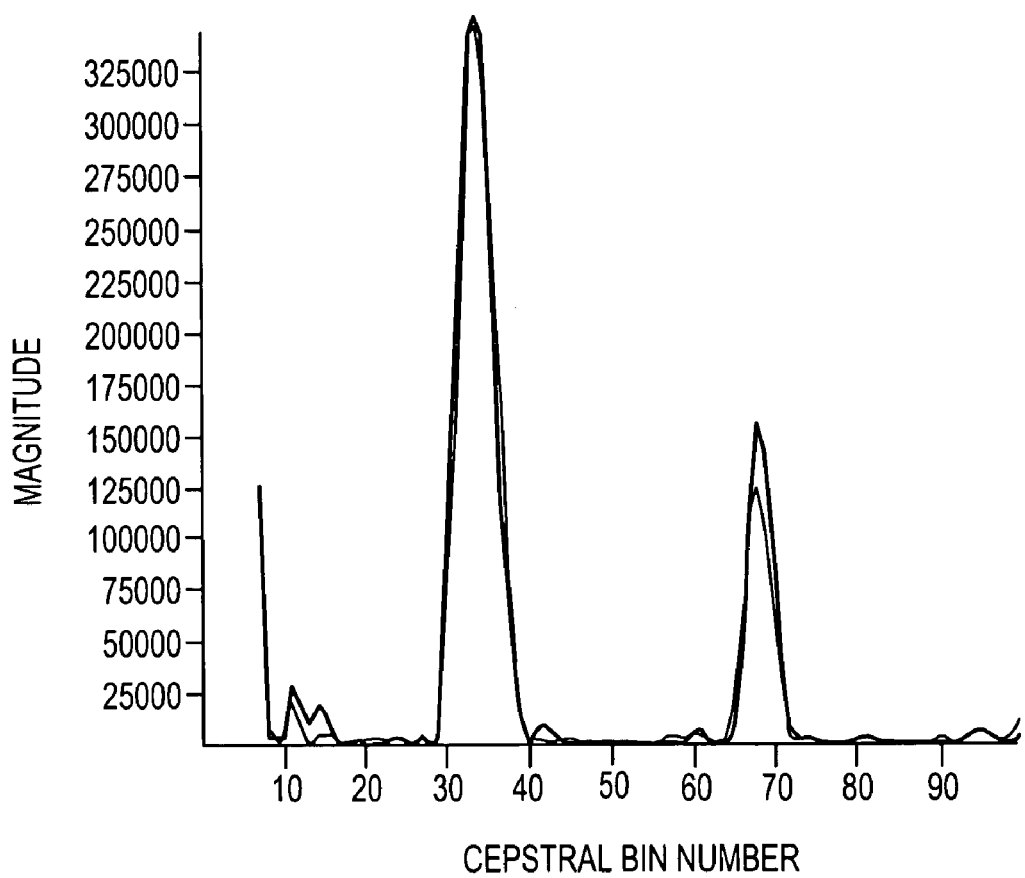
FIG. 5E is a plot showing red and infrared cepstrums corresponding to the typical red and infrared time domain plethysmographic input signals shown in FIG. 5A.
Figure 6B:
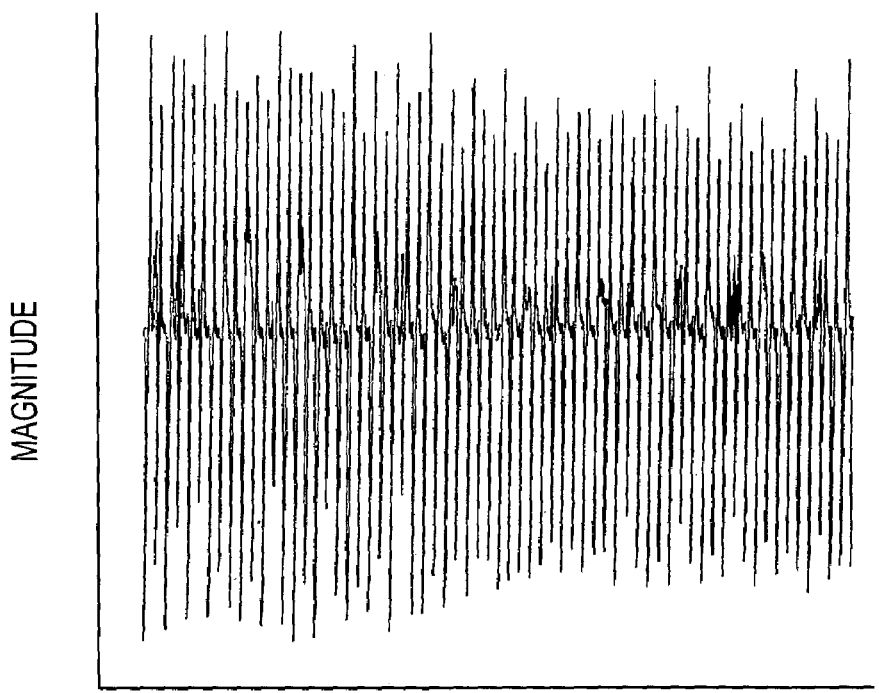
FIG. 6B is a plot showing differentiated waveforms obtained from the typical red and infrared time domain plethysmographic input signals shown in FIG. 6A.
Figure 6C:
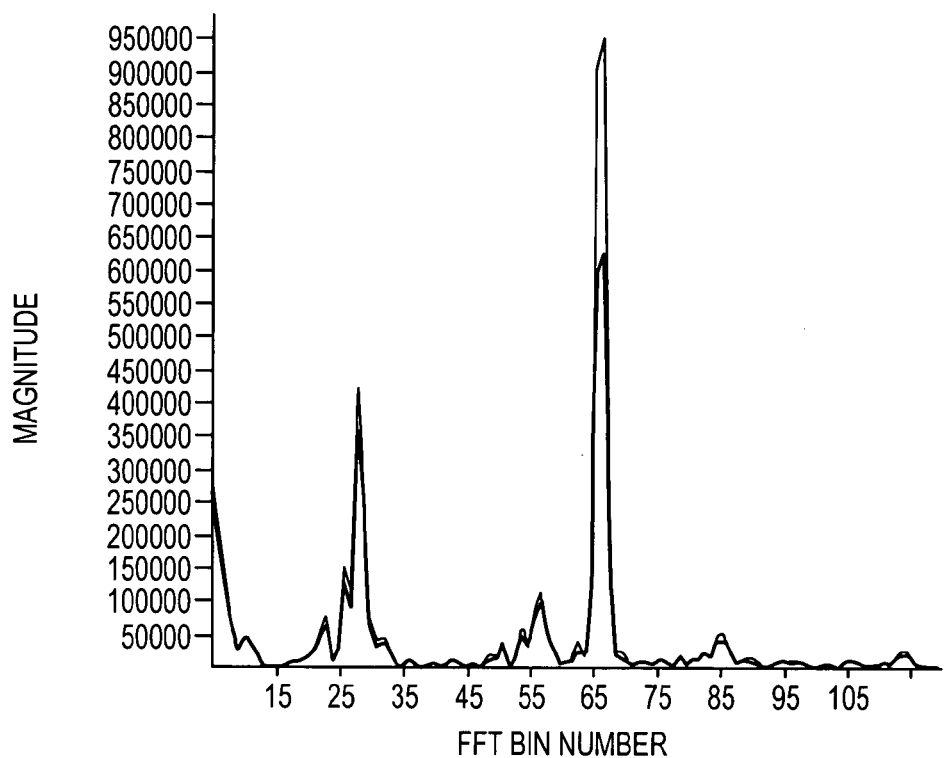
FIG. 6C is a plot showing red and infrared energy spectra corresponding to the typical red and infrared time domain plethysmographic input signals shown in FIG. 6A.
Figure 6D:
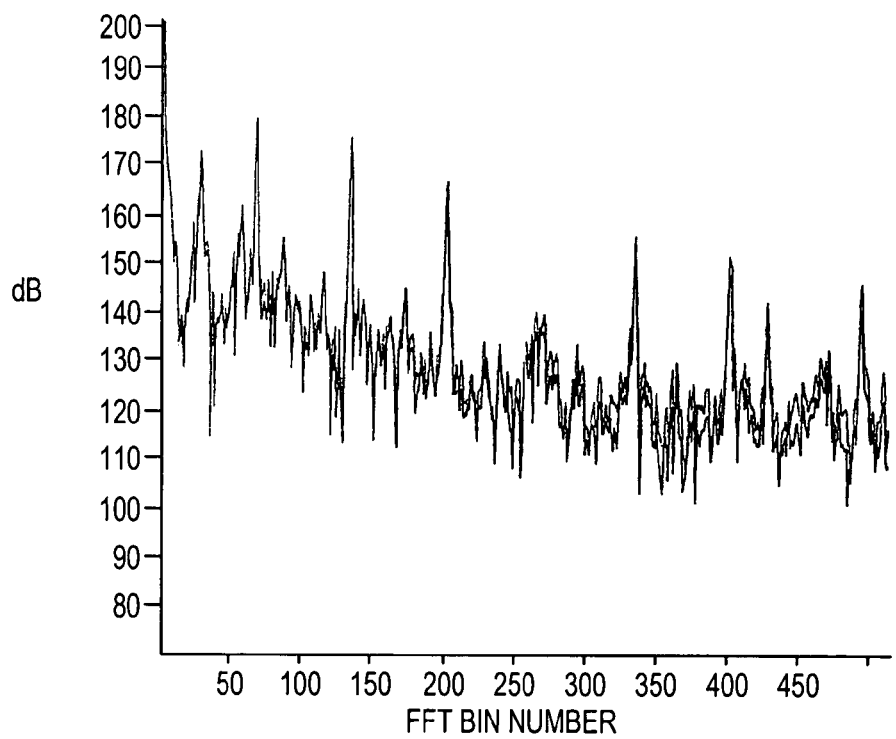
FIG. 6D is a plot showing red and infrared log spectra corresponding to the typical red and infrared time domain plethysmographic input signals shown in FIG. 6A.
Figure 6E:
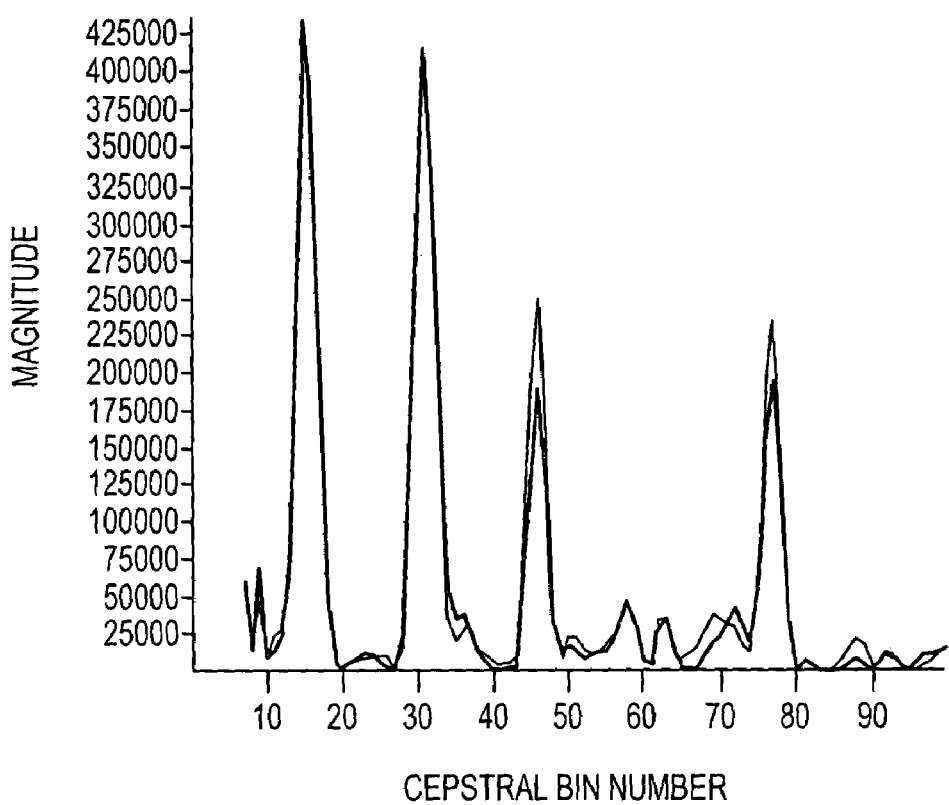
FIG. 6E is a plot showing red and infrared cepstrums corresponding to the typical red and infrared time domain plethysmographic input signals shown in FIG. 6A.

The digitized time domain red and infrared plethysmographic signals are smoothed (420) via a suitable smoothing window (e.g. Hanning, Hamming, or Kaiser) and are then processed in parallel via a complex FFT (430). The output from the first stage FFT is then decoded and the separate red and infrared energy spectra and log power spectra are computed and stored (440, 450). Plots of red and infrared energy spectra and log spectra obtained for the red and infrared signals of FIGS. 5A and 6A are shown in FIGS. 5C and 5D, respectively, and in FIGS. 6C and 6D, respectively. A second stage FFT (460) is then applied to the log power spectra to obtain red and infrared cepstra (470) therefrom. If desired, the results of the first and second stage FFT calculations may be scaled to help prevent floating point errors in subsequent computations. Plots of the red and infrared cepstra obtained for the red and infrared signals of FIGS. 5A and 6A are shown in FIGS. 5E and 6E. Peaks in the cepstra (which has the dimension of Quefrency) are examined (480) and transformed to provide an estimate of pulse frequency.

The cepstral based pulse rate estimate is provided to a pulse arbitration module (490). The pulse arbitration module (490) also receives estimates of the patient's pulse rate based on examination of peaks in the energy spectra and log power spectra. Additionally, a time-domain pulse rate estimate is extracted (500) from the digitized time domain red and infrared plethysmographic signals via a conventional technique such as differentiation, thresholding and picking the most commonly found interval. Plots of the differentiated waveforms obtained from the time domain red and infrared plethysmographic signals of FIGS. 5A and 6A are shown in FIGS. 5B and 6B. The time domain based pulse rate estimate is also provided as an input to the pulse arbitration module (490).

Information relating to the peaks of the energy spectra and the cepstra are input to a motion classification and motion strength estimation module (510). The motion classification and motion strength estimation module (510) uses both the amplitude, relative position and spacing of the respective peaks in the red and infrared energy spectra and cepstra to make motion classification and strength judgments. A simple measure classification and motion estimation can be derived by the number and spacing of cepstral peaks. In this regard, a relatively clean plethysmographic signal will typically produce one major cepstral peak. As the number and size of the cepstral peaks increases, sizable motion components can be inferred. Information from the motion classification and motion strength estimation module (510) is input to both an adaptive filter module (520) and the pulse arbiter module (490).

Figure 5F:
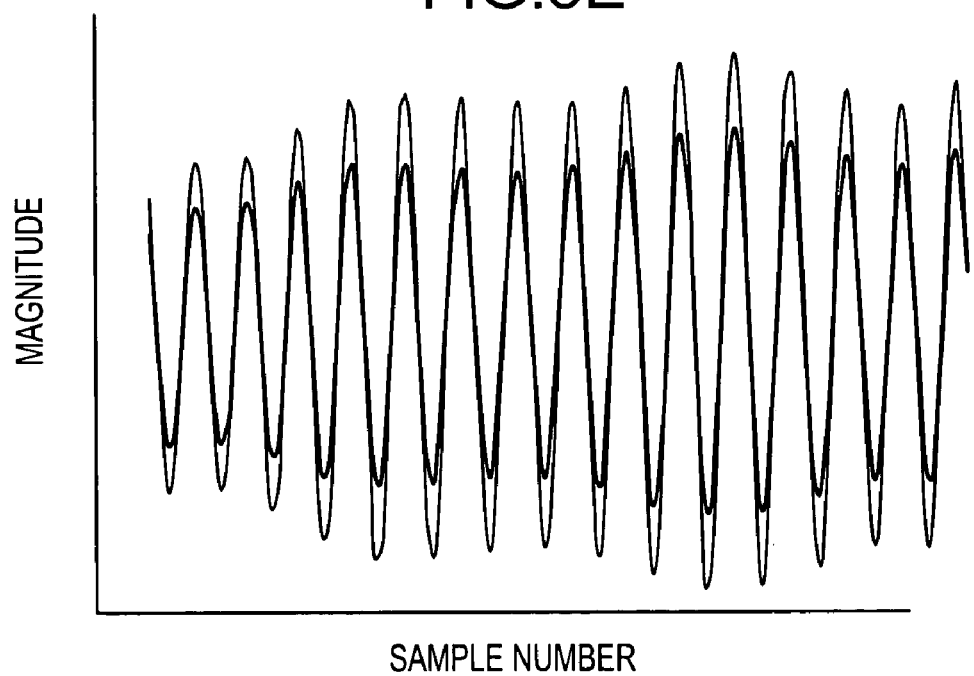
FIG. 5F is a plot showing frequency domain filtered red and infrared plethysmographic waveforms corresponding to the typical red and infrared time domain plethysmographic input signals shown in FIG. 5A.
Figure 6F:
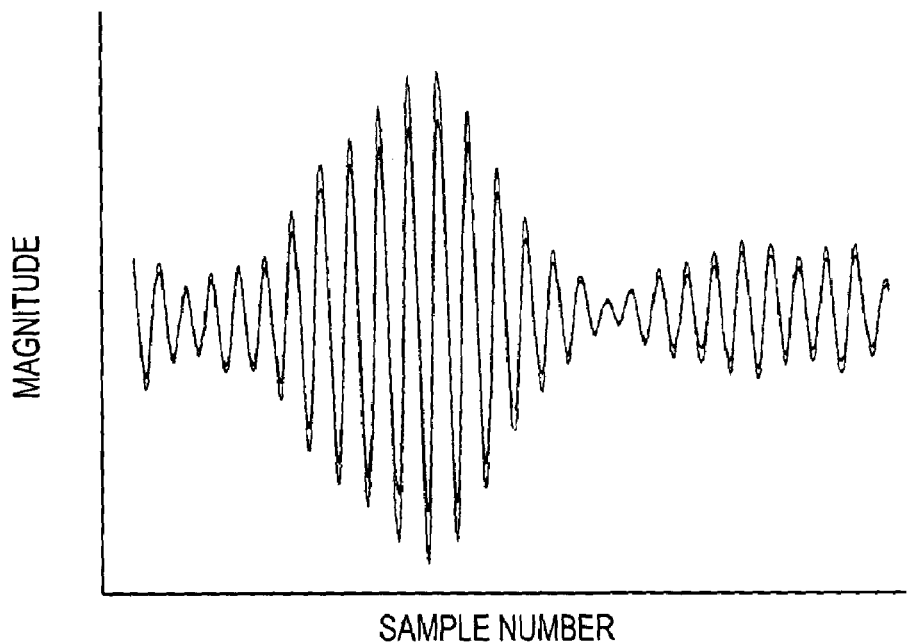
FIG. 6F is a plot showing frequency domain filtered red and infrared plethysmographic waveforms corresponding to the typical red and infrared time domain plethysmographic input signals shown in FIG. 6A.

The adaptive filter module (520) uses estimates of the pulse frequency and the frequency distribution of the motion noise components (if present) to control filtering in the frequency domain in order to improve the signal to noise ratio of the pulse fundamental frequency components and/or its harmonics. In this regard, the red and infrared frequency domain plethysmographic signals obtained after the first stage FFT (430) signals are filtered (530) to produce filtered frequency domain red and infrared plethysmographic signals. Plots of the filtered frequency domain red and infrared plethysmographic signals corresponding to the time domain red and infrared plethysmographic signals of FIGS. 5A and 6A are shown in FIGS. 5F and 6F. A number of different types of filters may be implemented including both finite impulse response (FIR) and infinite impulse response (IIR) filters. One disadvantage of spectral methods is that they are not suited for tracking rapid changes in the input signal. However in the present method (400) the spectral information is used to control an adaptive filter. By using time domain pulse measurement techniques on the output signal from this filter, the ability to track reasonably fast changes is achieved.

An inverse FFT operation (540) is performed to obtain filtered time domain red and infrared plethysmographic signals, and an overlap and add operation (550) is performed to reconstruct the plethysmographic signals minus the DC components and with reduced motion components. Following the overlap and add operation (550), the energy content for both the red and infrared filtered signals is then obtained (560) via, for example, a root-mean-square (rms) measure. This provides an estimate of the AC red and infrared levels. Although not shown in FIG. 4, it is also possible to obtain an estimate of the red and infrared AC levels via the cepstral domain. The main peak location of the red and infrared cepstra can be translated to a frequency value and the value of the energy for that frequency and its harmonics can be obtained (i.e., integrated) by referring to the stored energy spectrum for the red and infrared signals. It is also feasible to use the relative amplitudes of the red and infrared cepstral peaks to derive an AC estimate. Following the overlap and add operation (550), another conventional time domain based pulse estimation is also performed (570) on the filtered red and infrared signals and this estimate is also sent to the pulse arbiter module (490).

The pulse arbiter (490) uses the various time domain, filtered time domain, energy spectra, log power spectra and cepstral based pulse estimates and the motion strength and classification to provide an overall best estimate (580) of the patient's pulse rate. In this regard, for a range of motions the location of the major cepstral peak suffices as a good estimate of pulse frequency. However for large motion amplitudes and motion that produces waveforms similar to those of red and infrared plethysmographic signals it is necessary to examine a number of parameters to resolve competing estimates. More particularly, the pulse arbitration module (490) examines the correlation between the time domain (both filtered and unfiltered), spectral domain (both energy and log power) and cepstral domain based pulse estimates and uses the motion estimation derived from the cepstrum in the motion classification and motion strength estimation module (510) to weight the respective pulse rate estimates. If significant motion is present then cepstral information can be used to resolve between competing spectral pulse candidates. In this regard, the typical pulse waveform which is 'sawtoothed shaped' would result in a main fundamental spectral peak with usually at least two visible harmonic peaks. The resulting cepstra would be one main peak associated with the fundamental frequency. Therefore spectral candidates with no corresponding cepstral peak can be eliminated. Further, in cases where there is competing noise around the fundamental frequency peak, a cepstral peak can be confirmed by examining the energy or log spectra for a fundamental frequency peak and related harmonics. In addition to the previously described pulse arbitration process (490), it would also be feasible to employ a neural-net for the pulse arbitration process (490).

Another strategy that may be employed in the pulse arbiter module (490) is to relate the cepstral peak to a region or channel in the energy spectrum and to obtain an AC value and then derive a SPO2 estimate. This SPO2 estimate can be referred to another SPO2 estimate derived from the mean energy over the allowable pulse range (e.g., 30–350 bpm). A valid cepstral candidate will generate a similar track of SPO2 over time as the estimate derived from mean energy. This information can also be used to resolve amongst competing cepstral candidates for the one related to the pulse frequency.

In addition to obtaining an overall best estimate (580) of the patient's pulse rate, the plethysmographic signal processing method (400) of FIG. 4 also derives an estimate of the patient's SPO2 level. The energy content of the time domain red and infrared plethysmographic signals is obtained (590) via, for example a root mean square (rms) transform. This provides an estimate of the red and infrared DC levels. The red and infrared DC levels (590) and AC levels (560) are provided to an SPO2 module (600). As discussed in more detail above in connection with step (310) of the method (200) of FIG. 2, the SPO2 module (600) uses the red and infrared DC and AC levels to derive a measure that can be correlated with the patient's SPO2 level in a manner similar to conventional regression based techniques.

The cepstral domain plethysmographic signal processing method (400) of FIG. 4 also provides for obtaining an enhanced perfusion index (PI) measure when motion artifacts are present in the red and infrared time domain plethysmographic signals as compared to known time domain based perfusion index measures. The perfusion index is a measure of relative perfusion in the patient tissue site and is indicative of pulse strength. A time-domain based perfusion index measure may be obtained by, for example, calculating normalized plethysmographic signal amplitudes for the red and infrared time domain plethysmographic signals by summing the normalized delta amplitudes covering the rising portion of one cycle of the pulse waveform. This value can be termed Snda. In this regard, the perfusion index may be calculated from the red and infrared Snda values in accordance with the following expression:

$$PI = (Snda \text{ (red)} * 0.0563 + Snda \text{ (infrared)} * 0.3103)$$
*Scaling Factor Further detail regarding such a known time domain based method for obtaining a perfusion index measure is described in U.S. Pat. No. 5,766,127 entitled "METHOD AND APPARATUS FOR IMPROVED PHOTOPLETHYSMOGRAPHIC PERFUSION-INDEX MONITORING", the entire disclosure of which is incorporated herein.

However it is also possible to obtain a measure of the red and infrared plethysmographic signal amplitudes from their respective energy spectrums when the frequency components present in the energy spectrums due to the pulse signal can be identified via processing of the red and infrared cepstrums. In the regard, the plethysmographic signal processing method (400) may incorporate a perfusion index estimator step (610) wherein the red and infrared cepstrums obtained in step (470) are used to identify the frequency components present in the red and infrared energy spectrums obtained in step (440) that are associated with the pulse rate of the patient (i.e. the fundamental pulse frequency and its harmonics). The perfusion index estimator module (610) computes normalized amplitudes for the identified red and infrared spectral peaks. A perfusion index value (620) may then be computed from the normalized amplitudes of the identified red and infrared spectral peaks in accordance with, for example, the following expression:

$$PI=(ESamp\ (red)*0.0563+ESamp(infrared)+0.3103)\\*ESscaling$$

where ESamp(red) and ESamp(infrared) are the normalized amplitudes derived from the identified spectral peaks in the red and infrared energy spectrums and ESscaling is a scaling factor adjusted to give the spectral PI measure an equivalent value to the time domain PI measure. Because the spectral PI measure uses normalized amplitudes of the identified peaks in the red and infrared spectrums associated with the fundamental pulse frequency, the spectral PI measure is less susceptible to corruption by motion artifacts present in the time domain plethysmographic signals since peaks associated with motion artifacts will be ignored when identifying the fundamental pulse frequency peaks using the cepstrums.

Where desired, the spectral based PI measure may be correlated with the time domain based PI measure to provide a single PI measure. Further the spectral based PI measure provides information that can be used in tracking and identification of the fundamental pulse frequency by the pulse arbitration module (490). In this respect a spectral PI measure may be calculated for each spectral candidate and these estimates can be used in a scoring and arbitration scheme to track and resolve the correct (pulse produced) fundamental pulse frequency candidate.

While various embodiments of the present invention have been described in detail, further modifications and adaptations of the invention may occur to those skilled in the art. However, it is to be expressly understood that such modifications and adaptations are within the spirit and scope of the present invention.

What is claimed is:

1. A method of processing at least first and second plethysmographic signals obtained from a patient, the first and second plethysmographic signals being obtained in a first domain, said method comprising the steps of:

transforming the first and second plethysmographic signals from the first domain to a second domain different from the first domain to obtain first and second plethysmographic signals in the second domain;

applying log transformations to the first and second plethysmographic signals in the second domain to obtain first and second log transformed plethysmographic signals in the second domain;

transforming the first and second log transformed plethysmographic signals in the second domain to a third domain different from the first and second domains to obtain first and second plethysmographic signals in the third domain;

examining at least the first and second plethysmographic signals in the third domain to obtain information therefrom relating to a physiological condition of the patient, wherein said step of examining at least the first and second plethysmographic signals in the third domain comprises identifying a peak in the first plethysmographic signal in the third domain associated with a pulse rate of the patient and identifying a peak in the second plethysmographic signal in the third domain associated with a pulse rate of the patient;

determining a DC level of the first plethysmographic signal in the second domain;

determining a DC level of the second plethysmographic signal in the second domain;

obtaining an AC level of the first plethysmographic signal in the first domain from the identified peak in the first plethysmographic signal in the third domain;

obtaining an AC level of the second plethysmographic signal in the first domain from the identified peak in the second plethysmographic signal in the third domain; and computing a value correlated with a blood analyte level of the patient from the DC levels of the first and second plethysmographic signals in the second domain and the AC levels of the first and second plethysmographic signals in the first domain.

2. The method of claim 1 wherein the first domain comprises the time domain, the second domain comprises the frequency domain, and the third domain comprises the cepstral domain.

3. The method of claim 1 wherein said step of transforming the first and second plethysmographic signals from the first domain to the second domain comprises:

performing a Fourier transformation on the first plethysmographic signal in the first domain; and performing a Fourier transformation on the second plethysmographic signal in the first domain.

4. The method of claim 3 wherein the Fourier transformations performed comprise fast Fourier transformations.

5. The method of claim 1 wherein said step of transforming the first and second log transformed plethysmographic signals from the second domain to the third domain comprises:

performing a Fourier transformation on the first log transformed plethysmographic signal in the second domain; and performing a Fourier transformation on the second log transformed plethysmographic signal in the second domain.

6. The method of claim 5 wherein the Fourier transformations performed comprise fast Fourier transformations.

7. The method of claim 1 wherein the physiological condition of the patient comprises a pulse rate of the patient and said method further comprising the step of:

estimating the pulse rate of the patient based on locations of the identified peaks in the first and second plethysmographic signals in the third domain.

8. The method of claim 1 wherein in said step of computing, the blood analyte level is an SPO2 level.

9. The method of claim 1 further comprising:

transmitting a red wavelength optical signal through a tissue site of the patient to obtain the first plethysmographic signal in the first domain; and transmitting an infrared wavelength optical signal through the tissue site of the patient to obtain the second plethysmographic signal in the first domain.

10. A method of determining a pulse rate of a patient from at least one plethysmographic signal obtained from the patient in a first domain, said method comprising the steps of:

obtaining a first domain based estimate of the pulse rate of the patient from the first domain plethysmographic signal;

transforming the first domain plethysmographic signal to a second domain plethysmographic signal, the second domain being different from the first domain;

obtaining a second domain based estimate of the pulse rate of the patient from the second domain plethysmographic signal;

transforming the second domain plethysmographic signal to a third domain plethysmographic signal, the third domain being different from the first and second domains;

obtaining a third domain based estimate of the pulse rate of the patient from the third domain plethysmographic signal; and determining a best estimate of the pulse rate of the patient based on at least the first, second, and third domain based estimates of the pulse rate of the patient.

11. The method of claim 10 wherein the first domain comprises the time domain and the second domain comprises the frequency domain.

12. The method of claim 10 wherein said step of transforming the first domain plethysmographic signal to a second domain plethysmographic signal comprises performing a Fourier transform operation on the first domain plethysmographic signal.

13. The method of claim 10 wherein said step of transforming the second domain plethysmographic signal to a third domain plethysmographic signal comprises performing a Fourier transform operation on the second domain plethysmographic signal.

14. A pulse oximeter comprising:
a first optical signal source operable to emit an optical signal characterized by a first wavelength;
a second optical signal source operable to emit an optical signal characterized by a second wavelength different than said first wavelength;
a drive system operable to cause operation of said first and second optical signal sources such that each of said first and second optical signal sources emit first and second optical signals, respectively, in accordance with a multiplexing method;
a detector operable to receive said first and second optical signals after said first and second optical signals are attenuated by a patient tissue site of a patient, said detector being further operable to provide an analog detector output signal representative of said attenuated first and second optical signals;
a digital sampler operable to sample the analog detector output signal at a desired sampling rate and output a digital signal having a series of sample values representative of said attenuated first and second optical signals; and
a digital processor enabled to demultiplex the series of sample values into first and second plethysmographic signals in a first domain, transform the first and second plethysmographic signals in the first domain into first and second plethysmographic signals in a second domain different than the first domain, apply log transformations to the first and second plethysmographic signals in the second domain to obtain first and second log transformed plethysmographic signals in the second domain, transform the first and second log transformed plethysmographic signals in the second domain into first and second plethysmographic signals in a third domain different than the first and second domains, and examine at least the first and second plethysmographic signals in the third domain to obtain information therefrom relating to a physiological condition of the patient, wherein the physiological condition of the patient comprises a pulse rate of the patient, and wherein said digital processor is further enabled to construct a second domain filter based at least on the pulse rate of the patient, filter the first and second plethysmographic signals in the second domain using the filter to obtain filtered first and second plethysmographic signals in the second domain, and transform the filtered first and second plethysmographic signals in the second domain into filtered first and second plethysmographic signals in the first domain.

15. The pulse oximeter of claim 14 wherein the first domain comprises the time domain and the second domain comprises the frequency domain.

16. The pulse oximeter of claim 14 wherein said first wavelength is within the range of infrared light wavelengths and said second wavelength is within the range of red light wavelengths.

17. The pulse oximeter of claim 14 wherein said digital processor is enabled to perform fast Fourier transforms on the first and second plethysmographic signals in the first domain to transform the first and second plethysmographic signals in the first domain into the first and second plethysmographic signals in the second domain.

18. The pulse oximeter of claim 14 wherein said digital processor is enabled to perform fast Fourier transforms on the first and second log transformed plethysmographic signals in the second domain to transform the first and second log transformed plethysmographic signals in the second domain into the first and second plethysmographic signals in the third domain.

19. The pulse oximeter of claim 14 wherein said digital processor is further enabled to determine DC levels of the first and second plethysmographic signals in the first domain, determine AC levels of the first and second filtered plethysmographic signals in the first domain, and compute a value correlated with a blood analyte level of the patient from the DC values of the first and second plethysmographic signals in the first domain and AC levels of the first and second filtered plethysmographic signals in the first domain.

20. The pulse oximeter of claim 19 wherein the blood analyte level is an SPO2 level.

* * * * *